(12) United States Patent
Ressel

(10) Patent No.: US 10,945,802 B2
(45) Date of Patent: Mar. 16, 2021

(54) PACKING SYSTEM FOR MEDICAL DISPOSABLE GLOVES WITH THE METHOD FOR EXTERNAL EXTRACTION REDUCING CONTAMINATION

(71) Applicant: Dorota Ressel, Apache Junction, AZ (US)

(72) Inventor: Dorota Ressel, Apache Junction, AZ (US)

(73) Assignee: Dorothy Ressel Intellectual Properties, Inc., Apache Junction, AZ (US)

( * ) Notice: Subject to any disclaimer, the term of this patent is extended or adjusted under 35 U.S.C. 154(b) by 0 days.

(21) Appl. No.: 15/887,962

(22) Filed: Feb. 2, 2018

(65) Prior Publication Data

US 2019/0239974 A1    Aug. 8, 2019

Related U.S. Application Data

(60) Provisional application No. 62/600,148, filed on Feb. 13, 2017.

(51) Int. Cl.
| | |
|---|---|
| *A61B 42/40* | (2016.01) |
| *B65D 83/08* | (2006.01) |
| *A61B 50/22* | (2016.01) |

(52) U.S. Cl.
CPC .............. *A61B 42/40* (2016.02); *A61B 50/22* (2016.02); *B65D 83/0805* (2013.01)

(58) Field of Classification Search
CPC ......... A61B 42/40; A61B 50/22; A61B 42/22; A61B 42/10; A61B 42/50; B65D 83/0805;
(Continued)

(56) References Cited

U.S. PATENT DOCUMENTS

| | | | | | |
|---|---|---|---|---|---|
| 2,023,542 | A | * | 12/1935 | Peck ...................... | B65D 5/16 221/45 |
| 3,064,652 | A | * | 11/1962 | Corcoran .................. | A61J 1/10 604/111 |

(Continued)

FOREIGN PATENT DOCUMENTS

| | | |
|---|---|---|
| GB | 2495023 A | 3/2013 |
| GB | 2510428 A | 8/2014 |

(Continued)

*Primary Examiner* — Rakesh Kumar
(74) *Attorney, Agent, or Firm* — Adam R. Stephenson, LTD.

(57) ABSTRACT

Implementations of a glove dispensing system may include a flexible bag having a sealed first end and a sealed second end, the sealed first end opposite the sealed second end, a first plurality of openings extending through the first sealed end, a second plurality of openings extending through the second sealed end, and a reclosable sealed opening extending through a sidewall of the flexible bag. A plurality of gloves may be included within the flexible bag. A cuff of a glove of the plurality of gloves may be exposed through the reclosable sealed opening when the reclosable sealed opening is in an open configuration. Implementations of a glove dispensing system may include a rack coupled to the flexible bag. The rack may include a plurality of springs configured to stretch the flexible bag between the sealed first end and the sealed second end of the flexible bag.

10 Claims, 3 Drawing Sheets

Figure 1:
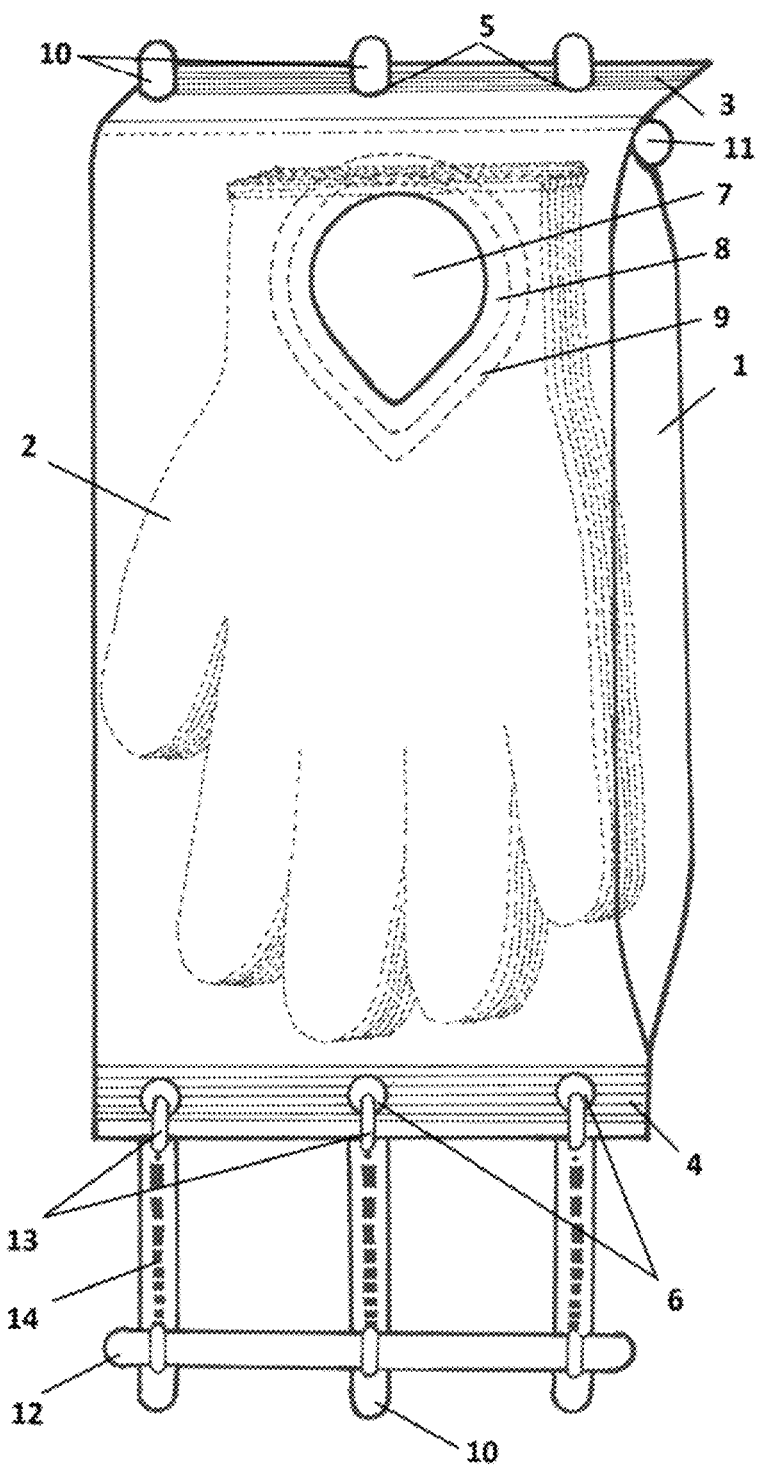

(58) Field of Classification Search
CPC .......... B65D 83/0835; B65D 83/0894; B65D 85/18; A41D 19/0055; A41D 19/015; A41D 16/0055
USPC ................................................ 221/307, 207
See application file for complete search history.

(56) References Cited

U.S. PATENT DOCUMENTS

| | | | | |
|---|---|---|---|---|
| 3,255,951 A * | 6/1966 | Kay | ........................ | B65D 33/08 383/10 |
| 3,281,056 A * | 10/1966 | Kugler | ................ | B65D 83/0805 206/554 |
| 3,306,492 A * | 2/1967 | Kugler | ................ | B65D 75/5894 221/63 |
| 3,312,339 A * | 4/1967 | Million | ................ | B65D 33/001 206/493 |
| 3,317,037 A * | 5/1967 | Russell | ................ | B65D 33/001 206/526 |
| 3,646,723 A * | 3/1972 | Meroney | ............ | B65B 67/1266 53/390 |
| 4,207,983 A * | 6/1980 | Wolske | .................. | B65D 29/04 206/526 |
| 4,216,863 A * | 8/1980 | Seymour-Smith | .......................... | B65D 75/5833 206/554 |
| 4,470,571 A * | 9/1984 | Hartman | ................ | A47B 19/10 248/452 |
| 4,537,330 A * | 8/1985 | Gelbard | ............... | B65D 33/001 221/26 |
| 4,550,856 A * | 11/1985 | Ballmann | ............... | A41D 13/11 128/202.13 |
| 4,611,719 A * | 9/1986 | Dudek | ..................... | B41J 11/58 211/50 |
| RE32,443 E * | 6/1987 | Kalal | ..................... | B65D 75/54 206/348 |
| 4,779,996 A * | 10/1988 | Sengewald | ............... | A45C 3/04 206/559 |
| 4,844,293 A | 7/1989 | McLaughlin | | |
| 4,988,213 A * | 1/1991 | Mattle | .................. | B65D 33/001 206/554 |
| 5,044,494 A | 9/1991 | Tamura | | |
| 5,100,000 A * | 3/1992 | Huseman | ........... | B65D 33/2508 206/554 |
| 5,131,564 A * | 7/1992 | Plonkey | .................... | A47F 1/08 206/355 |
| 5,386,910 A * | 2/1995 | Liss | ........................ | A47G 29/00 206/554 |
| 5,457,944 A * | 10/1995 | Lipes | ..................... | B65B 43/14 206/554 |
| 5,562,213 A * | 10/1996 | Wile | ..................... | A47F 13/085 206/554 |
| 5,655,682 A * | 8/1997 | Hoffrichter | .......... | B65D 33/001 206/554 |
| 5,816,440 A | 10/1998 | Shields et al. | | |
| 5,860,529 A * | 1/1999 | Smithson | ............... | A47F 13/085 206/554 |
| 5,862,944 A * | 1/1999 | Scherr | .................... | B65D 33/14 206/554 |
| 5,927,660 A * | 7/1999 | McNerney | ............ | A47F 13/085 206/554 |
| 5,941,392 A * | 8/1999 | Huang | ................ | B65D 33/001 206/554 |
| 5,954,432 A * | 9/1999 | Laudenberg | ........... | B65D 33/08 383/10 |
| 6,042,063 A * | 3/2000 | Kerr | .................... | B65B 67/1227 248/100 |
| 6,179,126 B1 * | 1/2001 | Smithson | ............... | A47F 13/085 206/554 |
| 6,264,035 B1 * | 7/2001 | Petrie | .................... | A47F 9/042 206/554 |
| 6,286,681 B1 * | 9/2001 | Wilfong, Jr. | ......... | B65D 33/001 206/554 |
| 6,325,243 B1 * | 12/2001 | Bennett | .................... | A47F 1/085 221/307 |
| 6,382,429 B1 * | 5/2002 | Yeh | ........................ | A47F 9/042 206/554 |
| 6,416,220 B1 * | 7/2002 | Fox | ........................ | B65D 29/04 206/554 |
| 6,578,729 B2 * | 6/2003 | Grinberg | ............ | A41D 19/0072 2/159 |
| 6,708,841 B2 | 3/2004 | Baughman | | |
| 7,063,233 B2 | 6/2006 | Jordan et al. | | |
| 7,150,374 B1 * | 12/2006 | Camps | .................. | B65D 25/04 220/9.1 |
| 7,163,339 B1 * | 1/2007 | Hefner | ................... | B65D 29/04 206/554 |
| 7,600,641 B2 * | 10/2009 | Burgess | ............. | B65D 75/5838 206/233 |
| 7,699,189 B2 | 4/2010 | Tramontina | | |
| 8,016,111 B2 * | 9/2011 | Wilson | .................. | A45F 5/1046 206/554 |
| 8,067,072 B2 * | 11/2011 | Tan | ...................... | B65D 33/001 428/35.7 |
| 8,104,959 B2 * | 1/2012 | Lucas | ...................... | B65B 7/02 383/10 |
| 8,550,717 B2 * | 10/2013 | Hefner | ................... | B65D 33/01 383/117 |
| 8,567,618 B2 * | 10/2013 | Tan | ........................ | B65B 43/14 211/85.15 |
| 8,857,134 B2 * | 10/2014 | Lucas | ...................... | B65B 7/02 53/467 |
| 8,985,338 B2 * | 3/2015 | Fux | ........................ | B65B 63/02 206/756 |
| 9,630,375 B2 * | 4/2017 | Frei | ........................ | B32B 5/10 |
| 9,770,123 B2 * | 9/2017 | Tan | ........................ | A47F 9/042 |
| 10,144,575 B2 * | 12/2018 | Tan | .................. | B65D 83/0805 |
| 10,207,858 B2 * | 2/2019 | Tan | .................. | B65D 75/5827 |
| 10,390,635 B2 * | 8/2019 | Zender | ................ | B65D 33/065 |
| 10,479,541 B2 * | 11/2019 | DeMatteis | .......... | B65B 67/1227 |
| 2001/0023873 A1 * | 9/2001 | Wile | ........................ | A47F 5/01 221/26 |
| 2002/0139811 A1 * | 10/2002 | Tramontina | ......... | A47K 10/424 221/197 |
| 2003/0116580 A1 | 6/2003 | Baughman | | |
| 2004/0035896 A1 * | 2/2004 | Lapace | ................... | D06F 89/02 223/37 |
| 2005/0103679 A1 * | 5/2005 | Smithson | ............. | B65D 33/001 206/554 |
| 2005/0105832 A1 * | 5/2005 | Trinko | ................... | B65D 31/12 383/84 |
| 2005/0147331 A1 * | 7/2005 | Sway | ..................... | B65D 33/14 383/117 |
| 2006/0065680 A1 * | 3/2006 | LaPace | ................... | D06F 89/02 223/37 |
| 2006/0072856 A1 * | 4/2006 | Su | .......................... | B65D 33/14 383/8 |
| 2006/0102809 A1 * | 5/2006 | Broeders | ............. | B65B 67/1266 248/95 |
| 2006/0215941 A1 * | 9/2006 | Golbert | ............... | B65D 33/001 383/8 |
| 2007/0215630 A1 * | 9/2007 | Tramontina | ........ | B65D 83/0817 221/46 |
| 2008/0277308 A1 * | 11/2008 | Simhaee | .............. | B65D 33/1608 206/554 |
| 2009/0268990 A1 * | 10/2009 | Wilson | ................... | A45F 5/1046 383/13 |
| 2011/0293203 A1 * | 12/2011 | Wilson | .................... | A45C 3/04 383/13 |
| 2012/0160732 A1 * | 6/2012 | Tan | ...................... | B65D 33/007 206/554 |
| 2012/0298689 A1 | 11/2012 | Cohen | | |
| 2013/0200093 A1 * | 8/2013 | Carlson | ................ | B65D 75/56 221/1 |
| 2013/0248554 A1 * | 9/2013 | Robin | .................. | B65D 85/671 221/185 |
| 2014/0061220 A1 | 3/2014 | Kowal | | |
| 2015/0072849 A1 * | 3/2015 | Tan | ........................ | B31B 70/14 493/204 |

(56) References Cited

U.S. PATENT DOCUMENTS

| | | | |
|---|---|---|---|
| 2015/0081003 A1* | 3/2015 | Wainwright | B05D 1/18 623/1.11 |
| 2015/0108158 A1* | 4/2015 | Tan | B65D 83/0805 221/64 |
| 2015/0266655 A1* | 9/2015 | Duffy | A41D 13/11 221/47 |
| 2016/0143490 A1* | 5/2016 | Yamada | A47K 10/426 221/1 |
| 2016/0185508 A1* | 6/2016 | Tan | B65D 75/5827 221/45 |
| 2016/0302626 A1* | 10/2016 | D'Hiet | B65D 5/4208 |
| 2016/0304276 A1* | 10/2016 | Castro | B65F 1/062 |
| 2017/0055727 A1* | 3/2017 | Tan | A47F 13/085 |
| 2018/0037356 A1* | 2/2018 | DeMatteis | B65B 67/1227 |
| 2018/0099469 A9* | 4/2018 | Tan | B31B 70/14 |
| 2018/0111744 A1 | 4/2018 | Modha | B65D 85/18 |
| 2018/0140026 A1* | 5/2018 | Nijmeh | A41D 19/01529 |
| 2018/0162628 A1* | 6/2018 | Modha | B65D 83/0817 |
| 2018/0186552 A1* | 7/2018 | DeMatteis | B65B 5/06 |
| 2018/0318154 A1* | 11/2018 | Louwrens | B65D 85/18 |
| 2018/0362236 A1* | 12/2018 | Dieringer | B65D 83/0805 |
| 2019/0071239 A1* | 3/2019 | Tan | B65D 75/566 |
| 2019/0135527 A1* | 5/2019 | Tan | B65D 75/566 |
| 2019/0231096 A1* | 8/2019 | Bacallao | A47F 9/042 |
| 2019/0239974 A1* | 8/2019 | Ressel | A61B 42/40 |
| 2020/0094485 A1* | 3/2020 | Rabiea | B65D 33/007 |

FOREIGN PATENT DOCUMENTS

| | | | | |
|---|---|---|---|---|
| GB | 2519839 B | | 9/2015 | |
| GB | 2528242 A | * | 1/2016 | A61B 42/40 |
| GB | 2528242 A | | 1/2016 | |

\* cited by examiner

PACKING SYSTEM FOR MEDICAL DISPOSABLE GLOVES WITH THE METHOD FOR EXTERNAL EXTRACTION REDUCING CONTAMINATION

BACKGROUND

1. Technical Field

This invention relates to a method of packing and dispensing disposable gloves and includes the new container and the system for carrying out this method.

2. Background

Disposable gloves are used in many fields and it is in medicine and diagnostics that the necessity of preserving them in an aseptic state is particularly essential. Studies carried out at American hospitals and clinics show that on average at least 50% of disposable gloves used by personnel are contaminated and in the case of gloves extracted from boxes placed close to water sources this share reaches 75%. Use of gloves often gives a false sense of safety which also results in the personnel not recognizing the necessity of careful disinfection of the hands or the necessity of careful drying of the hands before inserting hands into the boxes that contain the gloves.

From the description of U.S. Pat. No. 6,708,841 B2 there is known a wall-mountable glove dispenser into which a box of gloves is placed which enables dispensing of gloves.

From the description of U.S. Pat. No. 7,063,233B2 there is known a glove dispenser which enables one-off dispensing of a selected number of gloves.

From the description of U.S. Pat. No. 5,044,494A there is known a packaging case for packing either left-hand or right: hand gloves.

From the description of U.S. Pat. No. 7,699,189B2 there is known a glove dispenser in which gloves are tilted towards the opening through which they are dispensed to facilitate the extracting of each glove. The dispenser is configured in such a manner that a portion of the glove protrudes from the opening making it easier to grip and pull out.

From the description of U.S. Pat. No. 4,844,293A there is known a box for thin disposable gloves where the design of the box makes it possible to pull out single gloves.

From the description of U.S. Pat. No. 5,655,682 there is known a system of dispensing products consisting of a package of disposable plastic sheets that can be removed from the package one at a time to unpack the articles, e.g. gloves.

From the description of U.S. Pat. No. 5,816,440 there is known a system of dispensing disposable gloves where it is only the cuff of a single glove that protrudes from the dispensing hole and extracting one glove results in pulling the cuff of the next glove outside.

From the description of Patent GB2495023 there is known a glove dispenser where gloves are pushed upwards to facilitate taking them out of the pack. Gloves are arranged in such a manner that they can be taken out by touching only the cuff.

None of the solutions described above protect the packed gloves in a sufficient manner nor is it easy to implement packaging in mass production.

SUMMARY

The method of protecting the protective gloves against contamination consists in placing at least one glove (2 of FIG. 1) in the container (1 of FIG. 1) made of waterproof material, preferably plastic, which is then sealed, whereas the cuff of at least one glove (2 of FIG. 3) is placed in the immediate vicinity of the glove removal hole (7 of FIG. 1), so that after detaching the closure, the glove (2 of FIG. 1) is gripped by the cuff. The container and the system used to implement this method is also the subject of the invention.

DESCRIPTION

This invention provides and shows that it is possible to develop a solution with less disadvantages of the systems known from the prior art and which can more easily accommodate automated mass production packaging.

This new method of protecting disposable gloves against contamination is special and characterized in that at least one glove is placed in a container of a waterproof material, preferably of a plastic, which then closes tightly and where the cuff of at least one glove is positioned near the opening hole for extracting gloves.

The internal surface of the container is coated with a biocidal substance.

The container for at least one glove is attached to a rack tilted at an angle relative to the ground where the opening hole for extracting gloves is oriented downwards and towards the ground.

The container for disposable gloves according to this invention is special and characterized in that it has an opening for extracting gloves where the opening is protected with a tight closing seal mechanism and at least one glove is placed in the container in such a manner that its cuff is near of the opening used for extracting gloves.

The area of the opening hole for extracting gloves is coated with a biocidal substance and the inside of the container is coated with a biocidal substance.

The glove container is made of a waterproof material which is preferably of a plastic.

The container is in the shape of a bag with permanent seals at the top and bottom parts and the exterior portion of the seals are perforated to enable attaching the container to the rack.

The dispensing system for disposable gloves according to this invention is special and characterized in that it comprises at least one container with at least one glove as well as a rack for attaching the container. The container is in the shape of a bag sealed at the top and bottom and is attached to the rack where both the top part and the bottom part of the bag are attached to the rack such that the bag is stretched between the fixing points. The container has a tightly closed and sealed opening hole, for extracting gloves, and where the glove cuff is in the immediate proximity of the opening hole.

The container attached to the rack is tilted in relation to the ground at an angle less than 90 degrees horizontal to the ground. It is advantageous when this angle is in the range between 30 and 50 degrees.

This invention has the opening hole for glove extracting oriented downwards.

The pulling of gloves from the container does not require inserting the hand inside the container and the force of gravity both facilitates extracting the glove and helps prevent impurities and water from getting inside the container and thus the risk of contaminating the gloves inside the container is reduced.

In one container there can be one glove or there can be more than one glove. The cuff of each glove is placed in the immediate proximity of the opening hole for extracting gloves so that the user extracting a glove only grips the cuff and does not touch the other parts of the glove. The opening hole for extracting gloves is sealable. The closing mechanism can be any closing mechanism known, such as glue-covered film, enabling the hole to be opened and closed multiple times.

The system can comprise more than one container stretched between the racks. The container is inclined to the horizontal at an angle less than 90 degrees. It is most advantageous when the angle is between 30 and 50 degrees. Such an inclination is optimal as it facilitates the pulling of gloves from the container. In this system, all gloves can be pulled out one at a time in a manner that reduces the risk of the glove being contaminated. The person extracting a glove only touches it with a bare hand at the cuff and after donning it on they can extract another glove and done it on the other hand. Gloves should be packed in such a manner that the cuff of each one of them should be at the height of the opening hole for extracting them. For gloves that differ from each other depending on whether they are intended for the right or the left hand, they should be packed alternately, or separate containers for right-hand gloves and for left-hand gloves can be used.

The container being made of plastic is designed to enable the coating of its internal surfaces, including the area of the opening hole, with biocidal substances, which additionally reduces the hazard of the gloves getting contaminated by microbes.

The rack for attaching containers is comprised of hooks on which to hang the containers. For this reason containers should have perforations where the hooks can be placed. It is also possible to use other types of attachments such as clips or clamps. The attachments (including hooks) are connected to the rack by means of a spring or another elastic connector. The rack for containers can be a rigid structure and can also be foldable.

The rack can be mounted on a wall or on a special stand. The rack is attached in such a manner that the container should be at an angle less than 90 degrees relative to the ground.

This glove removal invention and glove container invention together form a solution that enables more safe dispensing of disposable gloves in a manner that helps protect them from contamination. Due to this the risk of hospital infections, and/or diagnostic errors, resulting from glove contamination will be reduced.

Figure 2:
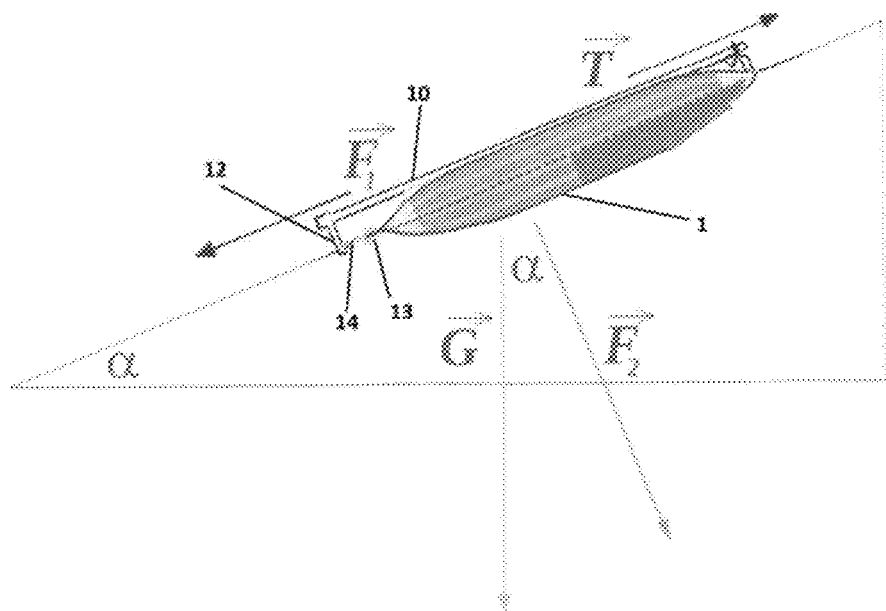
Figure 3:
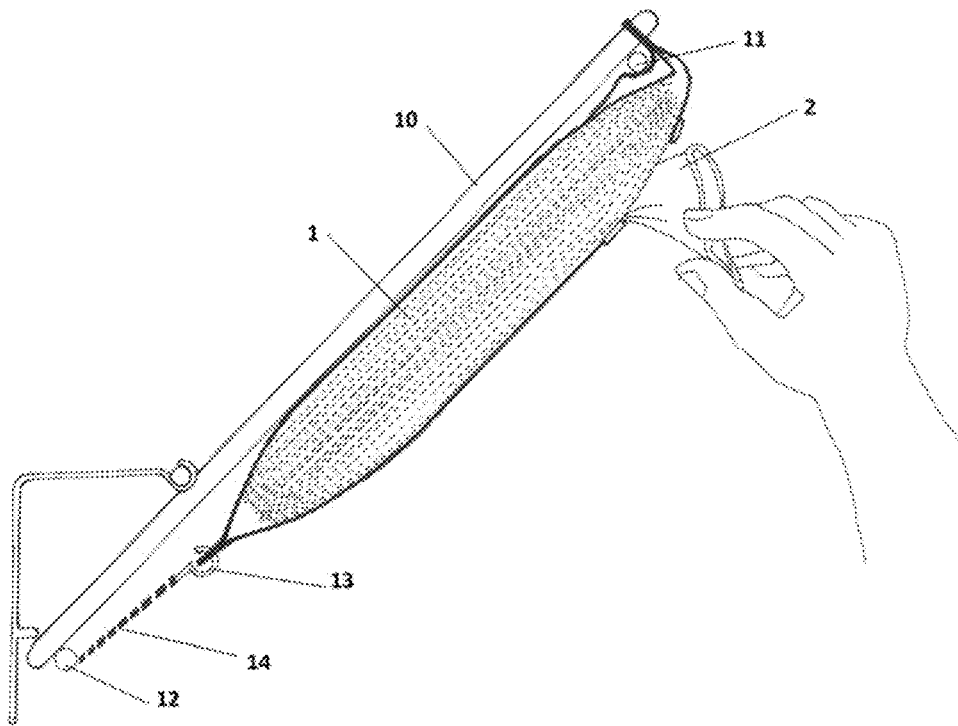
Figure 4:
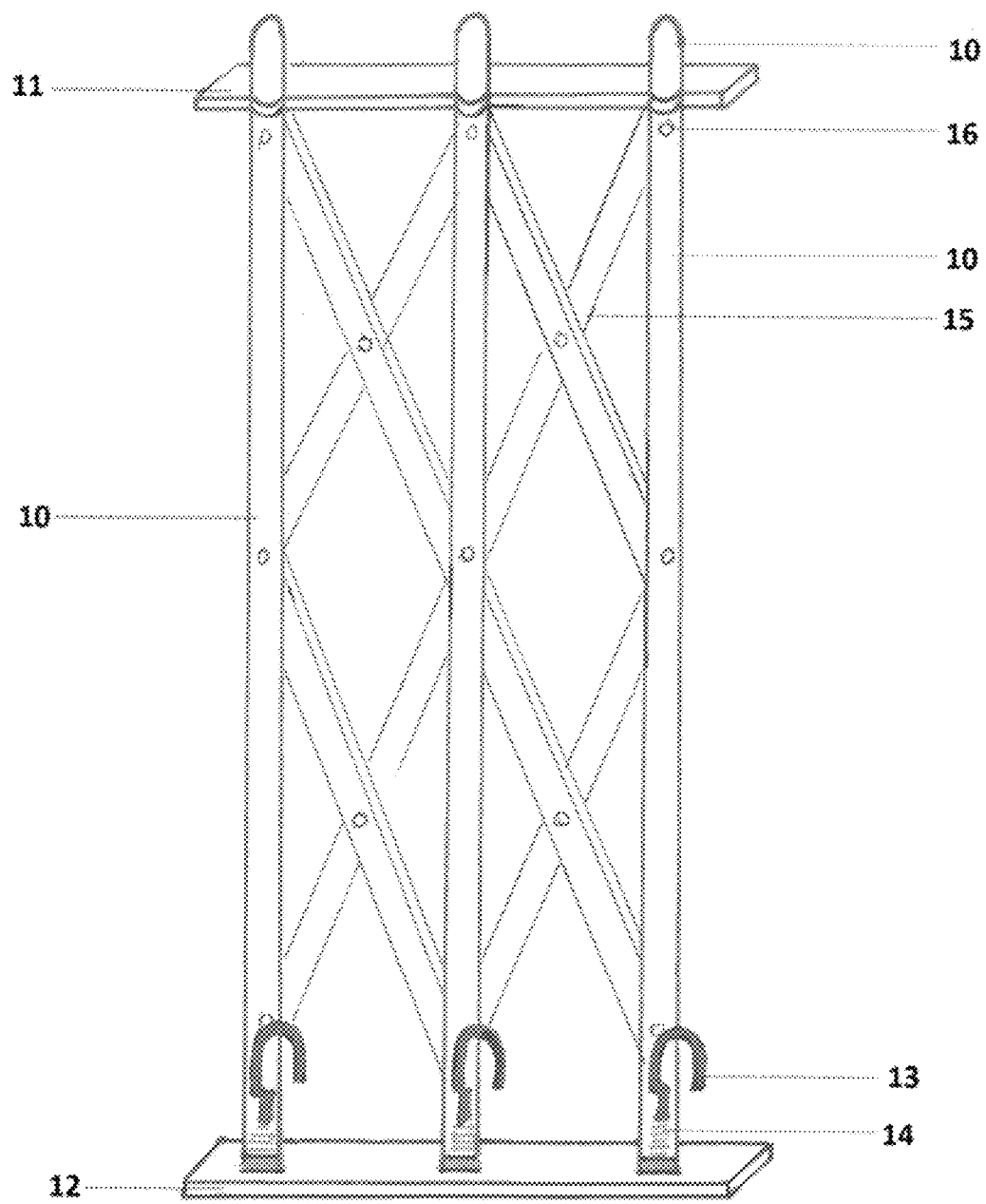

The object of the invention is shown in example drawings where FIG. 1 presents the container for gloves, FIG. 2 presents the container for gloves attached to the rack, FIG. 3 presents the manner of extracting gloves from the container, and FIG. 4 presents a foldable rack for containers.

Example, using FIG. 1 as reference:

The container (1) for disposable gloves (2) is made of a waterproof material which is advantageously of a plastic. Inside the container there are disposable gloves (2). The top part of the container (1) is sealed by means of a permanent seal (3) and the bottom part of the container (1) is also sealed by means of a permanent seal (4). These permanent seals (3 and 4) have perforations (5 and 6). In the top part of the container (1) there is an opening hole (7) for extracting the glove(s) (2). The external surface of the container (1), in the immediate proximity of the opening hole (7), is coated with glue (8) where to film (9) covering and securing the opening hole (7) is attached. Glue (8) is a type of glue which enables film (9) to be opened and closed multiple times. Vertical pillars (10) of the rack have the container (1) attached in such a manner that the ends of the poles are placed in the perforations (5). Container (1) rests on the horizontal bracket (11). At the bottom part of the rack there is a horizontal bracket (12) connected to the pillars (10). There are hooks (13) attached to bracket (12) through springs (14). The hooks (13) pass through the perforations (6).

At FIGS. 2 and 3 please see that the container (1) is attached to pillars (10) which are tilted at an angle (a) relative to the ground. The top part of the container (1) is attached to the pillars (10) and the bottom part (of the container) is attached to the bracket (12) by means of a system of hooks (13) with springs or elastic (14). The force of gravity (G) helps a glove to move freely downwards. The container is stretched on the rack and it is acted on by a force of tension (T). When a glove (2 FIG. 3) is pulled out of the container the container is additionally acted on by a force (F2 FIG. 2) and at the same time a force (F1) generated by the springs (14).

At FIG. 4 please see that the rack for attaching containers consists of vertical poles (10) and horizontal brackets (11 and 12). The bottom horizontal bracket (12) has hooks (13) attached to it on springs or elastic (14). The rack is reinforced with diagonal brackets (15) which are connected to the poles (10) by means of hardware connectors (16).

The invention claimed is:

1. A glove dispensing system comprising:
   a flexible bag comprising:
      a sealed first end and a sealed second end, the sealed first end opposite the sealed second end;
      a first plurality of openings extending through the first sealed end;
      a second plurality of openings extending through the second sealed end; and
      a reclosable sealed opening extending through a sidewall of the flexible bag;
   a plurality of gloves comprised within the flexible bag, wherein a cuff of a glove of the plurality of gloves is exposed through the reclosable sealed opening when the reclosable sealed opening is in an open configuration;
   a rack coupled to the flexible bag, the rack comprising a plurality of springs configured to stretch the flexible bag between the sealed first end and the sealed second end of the flexible bag.

2. The glove dispensing system of claim 1, wherein the plurality of springs are coupled to the second plurality of openings.

3. The glove dispenser system of claim 1, wherein the plurality of springs stretches the flexible bag and compresses the plurality of gloves between the inner sidewalls of the bag forming a seal between the inner sidewall of the bag and the glove exposed through the opening.

4. A glove dispensing system comprising:
   a flexible bag comprising:
      a sealed first end and a sealed second end;
      a first plurality of openings extending through the first sealed end;
      a second plurality of openings extending through the second sealed end; and
      an opening extending through a sidewall of the flexible bag;
   a plurality of gloves comprised within the flexible bag, wherein a cuff of a glove of the plurality of gloves is exposed through the opening when the opening is in an open configuration;

a rack coupled to the flexible bag, the rack comprising:
- a plurality of pillars extending substantially parallel to a longest length of the bag, wherein a first end of the plurality of pillars extend through the first plurality of openings;
- a plurality of springs coupled between the second plurality of openings and a second end of the plurality of pillars, the second end of the plurality of pillars opposite the first end of the plurality of pillars.

5. The glove dispenser system of claim 4, wherein the rack further comprises a plurality of brackets directly coupled to the plurality of pillars, wherein a longest length of each bracket of the plurality of brackets extends substantially perpendicularly to each pillar of the plurality of pillars.

6. The glove dispenser system of claim 4, wherein the rack further comprises a plurality of hooks coupled through the second plurality of openings and coupling the flexible bag to the plurality of springs.

7. The glove dispenser system of claim 4, further comprising a biocide coated on an interior of the flexible bag.

8. The glove dispenser system of claim 4, wherein the plurality of springs stretches the flexible bag and compresses the plurality of gloves between the inner sidewalls of the bag forming a seal between the inner sidewall of the bag and the glove exposed through the opening.

9. The glove dispenser system of claim 4, further comprising a plurality of angled cross supports between the plurality of pillars.

10. The glove dispenser system of claim 4, wherein the plurality of gloves are surgical gloves.

* * * * *